US012793363B2

United States Patent
(12) United States Patent
Teixido

(10) Patent No.: US 12,793,363 B2
(45) Date of Patent: Nov. 10, 2026

(54) SYSTEM AND METHOD FOR AUGMENTED REALITY VISUALIZATION OF BENIGN PAROXYSMAL POSITION VERTIGO (BPPV) DISORDER

(71) Applicant: Michael Teixido, Wilmington, DE (US)

(72) Inventor: Michael Teixido, Wilmington, DE (US)

(73) Assignee: Michael Teixido

( * ) Notice: Subject to any disclaimer, the term of this patent is extended or adjusted under 35 U.S.C. 154(b) by 165 days.

(21) Appl. No.: 18/944,562

(22) Filed: Nov. 12, 2024

(65) Prior Publication Data

US 2025/0182412 A1 Jun. 5, 2025

Related U.S. Application Data

(63) Continuation of application No. 17/638,523, filed as application No. PCT/US2020/048141 on Aug. 27, 2020, now Pat. No. 12,169,901.

(60) Provisional application No. 62/892,066, filed on Aug. 27, 2019.

(51) Int. Cl.

| | |
|---|---|
| ***G06T 19/00*** | (2011.01) |
| ***A61B 90/00*** | (2016.01) |
| ***G01S 17/89*** | (2020.01) |
| ***G06F 3/01*** | (2006.01) |
| ***G06T 7/246*** | (2017.01) |
| ***G06T 13/40*** | (2011.01) |
| ***G06T 19/20*** | (2011.01) |

(52) U.S. Cl.
CPC ............ *G06T 19/006* (2013.01); *A61B 90/36* (2016.02); *G01S 17/89* (2013.01); *G06F 3/012* (2013.01); *G06T 7/246* (2017.01); *G06T 13/40* (2013.01); *G06T 19/20* (2013.01); *A61B 2090/365* (2016.02); *G06T 2207/10016* (2013.01); *G06T 2207/10048* (2013.01); *G06T 2207/30196* (2013.01); *G06T 2210/41* (2013.01); *G06T 2219/2016* (2013.01)

(58) Field of Classification Search
None
See application file for complete search history.

(56) References Cited

U.S. PATENT DOCUMENTS

2013/0230837 A1* 9/2013 Meglan .................. G09B 23/28
434/262
2016/0262608 A1* 9/2016 Krueger ................. G16H 40/63

* cited by examiner

*Primary Examiner* — Robert J Craddock
(74) *Attorney, Agent, or Firm* — Smart & Biggar LP

(57) ABSTRACT

According to one aspect, a system for augmented reality visualization of benign paroxysmal position vertigo (BPPV) disorder. The system includes a camera configured to capture an image sequence, a processing unit configured to generate at least one virtual model of an inner ear, wherein the at least one virtual model of the inner ear comprises an accurate anatomical representation of a real human inner ear; and a display configured to display the at least one virtual model of the inner ear over the image sequence.

20 Claims, 7 Drawing Sheets

SYSTEM AND METHOD FOR AUGMENTED REALITY VISUALIZATION OF BENIGN PAROXYSMAL POSITION VERTIGO (BPPV) DISORDER

CROSS-REFERENCE TO RELATED APPLICATIONS

This application is a continuation of U.S. patent application Ser. No. 17/638,523 filed on Feb. 25, 2022, which is a 371 of International Application No. PCT/US2020/048141 filed on Aug. 27, 2020, which claims the benefit of U.S. Provisional Application No. 62/892,066 filed on Aug. 27, 2019, which is incorporated by reference herein in its entirety for all purposes.

FIELD

The described embodiments relate to a system and method for augmented reality visualization, and in particular, to a system and method for augmented reality visualization of benign paroxysmal position vertigo (BPPV) disorder.

Introduction

The following is not an admission that anything discussed below is part of the prior art or part of the common general knowledge of a person skilled in the art.

Benign paroxysmal position vertigo (BPPV) is a disorder which results from problems with the vestibular organs of the human inner ear. BPPV may result, for example, from any injury to the inner ear, illness in the inner ear, head injury (e.g., head concussions), as well as from old age. Individuals suffering from BPPV often experience short episodes of vertigo following specific head movements (e.g., head tilting and turning). The short episodes of vertigo may include, for example, false sensations of spinning, nausea, loss of balance, and vomiting.

SUMMARY OF THE VARIOUS EMBODIMENTS

According to one broad aspect of the invention, there is disclosed a system for augmented reality visualization of benign paroxysmal position vertigo (BPPV) disorder. The system includes a camera configured to capture an image sequence, a processing unit configured to generate at least one virtual model of an inner ear, wherein the at least one virtual model of the inner ear comprises an accurate anatomical representation of a real human inner ear, and a display configured to display the at least one virtual model of the inner ear over the image sequence.

In some embodiments, the display is configured to display the image sequence in real-time. In some embodiments the image sequence includes an image of a subject's head. In some embodiments, the at least one virtual model of the inner ear includes a set of virtual displaced otoconia.

In some embodiments, the at least one virtual model of the inner ear comprises a first virtual model of a right inner ear and a second virtual model of a left inner ear. In some embodiments, the processing unit is configured to transmit instructions for the display to display the first virtual model on a right side of the image of the subject's head, and the second virtual model on the left side of the image of the subject's head.

In some embodiments, the processing unit is further configured to monitor a movement of the subject's head in the image sequence, and is configured to generate a new orientation for at least one virtual model based on the monitored movement of the subject's head, and the display is configured to display the new orientation of at least one virtual model.

In some embodiments, the processing unit is further configured to monitor a movement of the display, and is configured to generate a new orientation for at least one virtual model of the inner ear based on the movement of the display.

In some embodiments, the virtual model of at least one inner ear is rotatable into a new orientation on the display.

In some embodiments, the processing unit is configured to generate a new position for the virtual displaced otoconia inside at least one virtual model of the inner ear, the new position for the displaced otoconia is based on the new orientation of at least one virtual model of the inner ear, and wherein the display is configured to display the new position of the virtual displaced otoconia.

In some embodiments, the processing unit is configured to code the virtual displaced otoconia with gravity properties, and is further configured to generate the new position for the virtual displaced otoconia based on the gravity properties.

In some embodiments, the processing unit is further configured to generate an augmented set of animated eyes, and the display is configured to display the augmented set of animated eyes over the image sequence.

In some embodiments, the augmented set of animated eyes is configured to follow a predetermined motion pattern based on a movement of the virtual displaced otoconia inside the virtual model of the inner ear.

In some embodiments, the processing unit is configured to monitor a movement of the subject's head in the image sequence based on a visual indicator located on the subject's head.

In some embodiments the processing unit is configured to monitor movement of a subject's head based on reading topographical features of the subject's head.

In some embodiments, the camera further comprises an infrared (IR) scanning capability.

In some embodiments, the processing unit is configured to monitor the movement of the subject's head in the image sequence based on information generated by the IR scanning capability of the camera.

According to another broad aspect, there is disclosed a method for generating an augmented reality model of at least one vestibular labyrinth. The method includes capturing an image sequence using a camera, using a processing unit, generating at least one virtual model of an inner ear, wherein the virtual model of the inner ear comprises an accurate anatomical representation of a real human inner ear, and displaying at least one virtual model of the inner ear over the image sequence.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

A preferred embodiment of the present invention will now be described in detail with reference to the drawings, in which.

Figure 1:
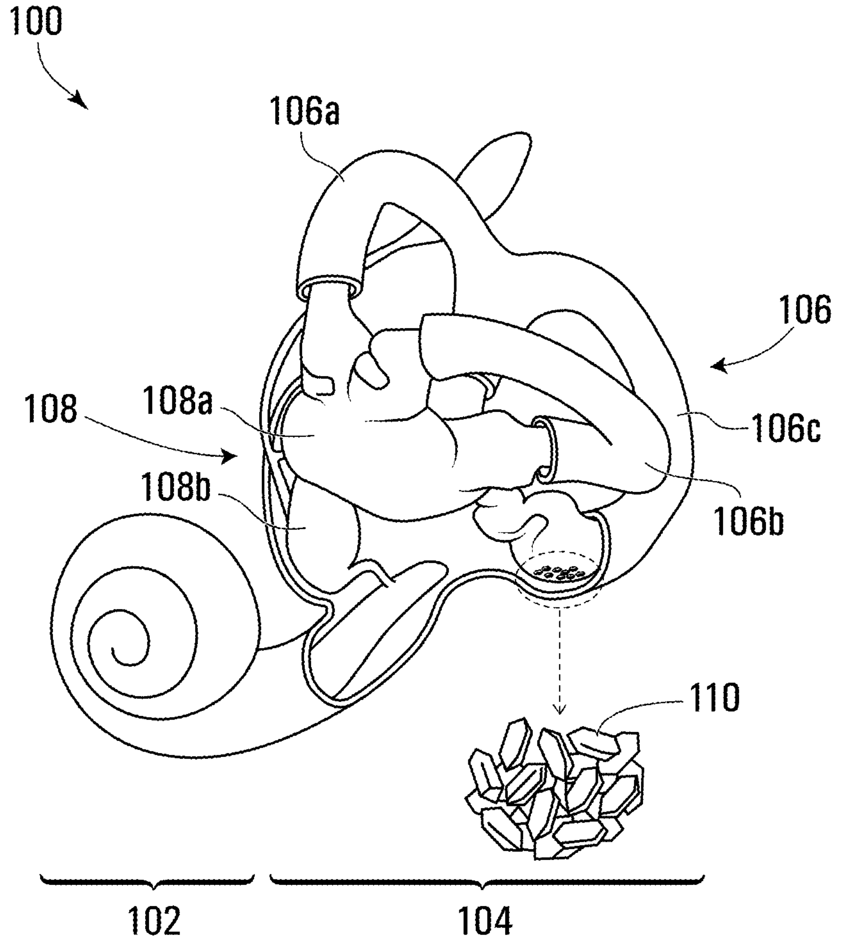
FIG. 1 is a schematic representation of the anatomy of an example human inner ear.

Further aspects and features of the example embodiments described herein will appear from the following description taken together with the accompanying drawings.

DETAILED DESCRIPTION OF THE EMBODIMENTS

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details, or with other methods, components, materials, etc. In other instances, well-known methods, procedures and components have not been described in detail since these are known to those skilled in the art. Furthermore, it should be noted that this description is not intended to limit the scope of the embodiments described herein, but rather as merely describing one or more exemplary implementations.

Unless the context requires otherwise, throughout the specification and claims which follow, the word “comprise” and variations thereof, such as, “comprises” and “comprising” are to be construed in an open, inclusive sense, that is as “including, but not limited to.”

It should be noted that terms of degree such as “substantially”, “about” and “approximately” when used herein mean a reasonable amount of deviation of the modified term such that the end result is not significantly changed. These terms of degree should be construed as including a deviation of the modified term if this deviation would not negate the meaning of the term it modifies.

Reference throughout this specification to “one embodiment” or “an embodiment” means that a particular feature, structures, or characteristics may be combined in any suitable manner in one or more embodiments.

As used in this specification and the appended claims, the singular forms “a,” “an,” and “the” include plural referents unless the content clearly dictates otherwise. It should also be noted that the term “or” is generally employed in its broadest sense, that is as meaning “and/or” unless the content clearly dictates otherwise.

The headings and Abstract of the Disclosure provided herein are for convenience only and do not interpret the scope or meaning of the embodiments.

The terms “coupled” or “coupling” as used herein can have several different meanings depending in the context in which these terms are used. For example, the terms coupled or coupling may be used to indicate that an element or device can electrically, optically, or wirelessly send data to another element or device as well as receive data from another element or device.

Similarly, throughout this specification and the appended claims the term “communicative” as in “communicative pathway,” “communicative coupling,” and in variants such as “communicatively coupled,” is generally used to refer to any engineered arrangement for transferring and/or exchanging information. Exemplary communicative pathways include, but are not limited to, electrically conductive pathways (e.g., electrically conductive wires, electrically conductive traces), magnetic pathways (e.g., magnetic media), optical pathways (e.g., optical fiber), electromagnetically radiative pathways (e.g., radio waves), or any combination thereof. Exemplary communicative couplings include, but are not limited to, electrical couplings, magnetic couplings, optical couplings, radio couplings, or any combination thereof.

Throughout this specification and the appended claims, infinitive verb forms are often used. Examples include, without limitation: “to detect,” “to provide,” “to transmit,” “to communicate,” “to process,” “to route,” and the like. Unless the specific context requires otherwise, such infinitive verb forms are used in an open, inclusive sense, that is as “to, at least, detect,” to, at least, provide,” “to, at least, transmit,” and so on.

The example embodiments of the systems and methods described herein may be implemented as a combination of hardware or software. In some cases, the example embodiments described herein may be implemented, at least in part, by using one or more computer programs, executing on one or more programmable devices comprising at least one processing element, and a data storage element (including volatile memory, non-volatile memory, storage elements, or any combination thereof). These devices may also have at least one input device (e.g. a keyboard, mouse, touchscreen, or the like), and at least one output device (e.g. a display screen, a printer, a wireless radio, or the like) depending on the nature of the device.

It should also be noted that there may be some elements that are used to implement at least part of one of the embodiments described herein that may be implemented via software that is written in a high-level computer programming language such as one that employs an object-oriented paradigm. Accordingly, the program code may be written in Java, C++ or any other suitable programming language and may comprise modules or classes, as is known to those skilled in object-oriented programming. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, EEPROM, magnetic disk, optical disc) or a device that is readable by a general or special purpose programmable device. The software program code, when read by the programmable device, configures the programmable device to operate in a new, specific and predefined manner in order to perform at least one of the methods described herein.

The description sets forth various embodiments of the systems, devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs executed by one or more computers (e.g., as one or more programs running on one or more computer systems), as one or more programs executed by on one or more controllers (e.g., microcontrollers) as one or more programs executed by one or more processors (e.g., microprocessors, central processing units, graphical processing units), as firmware, or as virtually any combination thereof, and that designing the circuitry and/or writing the code for the software and or firmware would be well within the skill of one of ordinary skill in the art in light of the teachings of this disclosure.

When logic is implemented as software and stored in memory, logic or information can be stored on any processor-readable medium for use by or in connection with any processor-related system or method. In the context of this disclosure, a memory is a processor-readable medium that is an electronic, magnetic, optical, or other physical device or means that contains or stores a computer and/or processor program. Logic and/or the information can be embodied in any processor-readable medium for use by or in connection with an instruction execution system, apparatus, or device, such as a computer-based system, processor-containing system, or other system that can fetch the instructions from the instruction execution system, apparatus, or device and execute the instructions associated with logic and/or information.

In the context of this specification, a "non-transitory computer-readable medium" can be any element that can store the program associated with logic and/or information for use by or in connection with the instruction execution system, apparatus, and/or device. The processor-readable medium can be, for example, but is not limited to, an electronic, magnetic, optical, electromagnetic, infrared, or semiconductor system, apparatus or device. More specific examples (a non-exhaustive list) of the computer readable medium would include the following: a portable computer diskette (magnetic, compact flash card, secure digital, or the like), a random access memory (RAM), a read-only memory (ROM), an erasable programmable read-only memory (EPROM, EEPROM, or Flash memory), a portable compact disc read-only memory (CDROM), digital tape, and other non-transitory media.

As discussed in the background, benign paroxysmal position vertigo (BPPV) is a disorder which results from problems with the vestibular organs of the human inner ear. BPPV may result, for example, from any injury to the inner ear, illness of the inner ear, head injury (e.g., head concussions), as well as from old age. Individuals suffering from BPPV often experience short episodes of vertigo that follow after specific head movements (e.g., head tilting and turning). The short episodes may include false sensations of spinning, nausea, loss of balance, and vomiting.

Referring now briefly to FIG. 1, there is shown a schematic representation of the anatomy of an example human inner ear 100. The schematic representation of the inner ear 100 is provided herein to allow for a more detailed discussion of BPPV.

The inner ear is generally composed of a spiral-shaped cochlea 102, and the vestibular labyrinth 104. The cochlea 102 is responsible for sound detection, while the vestibular labyrinth 104 is responsible for detecting linear and angular acceleration movement of the head.

The vestibular labyrinth 104 contains a number of sensory organs, including the semi-circular canals 106 and the otolith organs 108. The semi-circular canals 106 detect angular acceleration (e.g., rotational movement), and include the anterior canal 106*a*, the lateral canal 106*b*, and the posterior canal 106*c*. Each canal 106*a-c* is fluid-filled with endolymph fluid, and has an ampulla and a crista lined with microscopic sensory hair known as cilia. As the head experiences angular acceleration, the endolymph fluid moves within the canals and causes the cilia hairs to shift and transmit sensory signals to the brain.

In contrast, the otolith organs 108 assist in detecting linear acceleration movement of the head. As shown in FIG. 1, the otolith organs 108 include the utricle 108*a* and the saccule 108*b*. Each of the utricle 108*a* and the saccule 108*b* contains a mass of small bio crystals, known as otoconia, embedded in a gelatinous outer membrane of the otolithic organs. During linear acceleration of the head, the otoconia shift and cause sensory hair cells, also embedded in the gelatinous outer layer, to bend and transmit sensory signals back to the brain.

In general, BPPV occurs when the otoconia become dislodged, or displaced, from the otolithic membrane. The displaced otoconia subsequently migrate—under the force of gravity—into the semi-circular canals 106, and disrupt the normal functioning of the canals by making them sensitive to gravity. For example, small head movements can cause the otoconia 110 to shift inside the canals, under gravitational influence, and in turn, cause the cilia hairs to move, and transmit erroneous (or exaggerated) signals of head rotation to the brain. These signals contradict other sensory perceptions received by the brain (e.g., sight and hearing) and result in the temporary sensation of vertigo. The sensation of vertigo typically persists until the otoconia 110 re-settle inside the canals.

To diagnose and treat BPPV, experienced practitioners apply a sequence of head and body maneuvers to affected patients. The maneuvers guide the otoconia, using gravitational force, out of the canals and into a desired location within the inner ear. Practitioners often apply these maneuvers while observing specific patterns of involuntary eye movement in the patient. These patterns of eye movement, known as nystagmus, assist in identifying the ear which contains the moving otoconia, as well as the relative position within the ear where the otoconia are located. Accordingly, by observing the exhibited patterns of nystagmus, a practitioner may track the motion and position of the otoconia, and in turn, applying corrective maneuvers to guide the otoconia, inside the patient's ear, back into the otolithic organs.

Necessarily, caution must be exercised during the diagnosis and treatment of BPPV. In particular, an incorrect sequence of head and body maneuvers can aggravate the symptoms of BPPV in a patient. This, in turn, results in increased time and effort for performing remedial and corrective treatment to the patient.

To this end, it has been appreciated that there are currently few available tools which assist in-experienced practitioners (e.g., medical practitioners, or physical therapists) and students to better understand how to diagnose and treat cases of BPPV. For example, there are few assistive tools which help visualize movement of displaced otoconia inside the inner ear, as well as to visualize the relationship between nystagmus and the shifting of displaced otoconia within the ear. Still further, it has been also appreciated that little visual guidance is typically provided to practitioners while treating affected patients. For example, there are no readily available tools which visualize—in real-time or near real-time—the movement of otoconia inside a patient's ear as the practitioner is applying head and body maneuvers. It is accordingly expected that by providing practitioners with the ability to visualize movement of otoconia inside the ear, incidences of erroneous treatment may be greatly reduced.

In view of the foregoing, embodiments provided herein generally relate to a system and method for augmented reality (AR) visualization of benign paroxysmal position vertigo (BPPV) disorder. In particular, the system and method provided herein may allow for a better understanding of BPPV in subject patients.

Figure 2B:
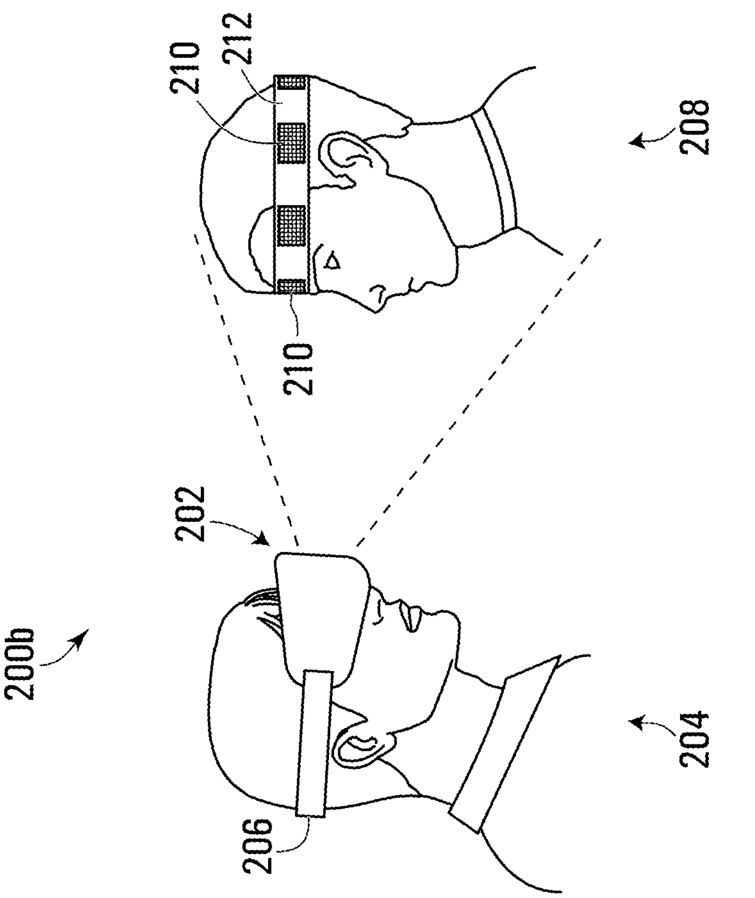
FIG. 2B is a schematic representation of an example environment for augmented reality visualization of BPPV, in accordance with some other embodiments.
Figure 2A:
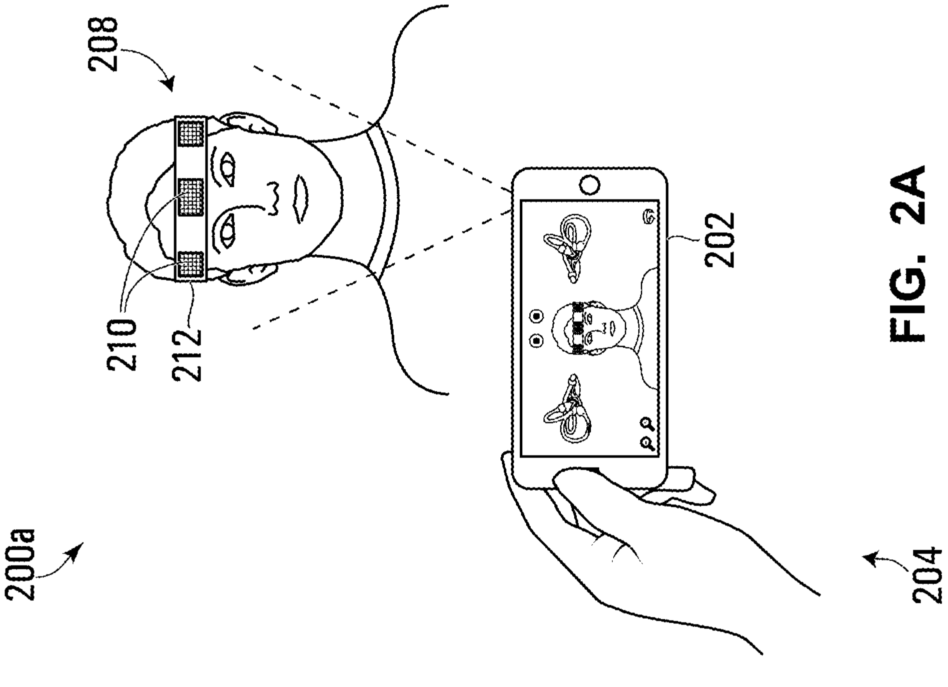
FIG. 2A is a schematic representation of an example environment for augmented reality visualization of BPPV, in accordance with some embodiments.

Referring now to FIG. 2A, there is shown a schematic representation of an example environment 200*a* for augmented reality visualization of BPPV, in accordance with some embodiments.

As shown, the environment 200*a* generally includes a user device 202 operated by a user 204. User 204 may be, for example, a medical practitioner, a physical therapist or a student. User 204 may use user device 202 to view an augmented reality visualization of BPPV.

Environment 200*a* may also include a subject 208. Subject 208 is, for example, a patient affected by BPPV, or otherwise, a test subject. The AR image displayed on user device 202 includes virtual objects (e.g., virtual inner ear models) projected over an image sequence (e.g., a digital video) of the subject 208, captured in real-time or near real-time by a camera in communication with user device 202. In some cases, user 204 and the subject 208 can be the same individual. For example, this can occur in cases where the user device 202 is used to self-diagnose, or self-treat BPPV.

In at least some embodiments, one or more visual indicators 210 are located, or positioned, over the subject's head 208. For example, as illustrated, the visual indicators 210 are attached to a head band 212 positioned around the subject's forehead. As explained herein, the visual indicators 210 can be used to detect the location of the subject's head in an image sequence captured by a user device camera. In particular, the visual indicators 210 can synchronize virtual objects displayed on the user device 202 with movement (e.g., rotation) of the subject's head in a captured image sequence. In some cases, a camera equipped with IR scanning functionality or otherwise, an application configured for image analysis, may also be used to detect the position of the subject's head in the captured image sequence. In these cases, the use of visual indicators 210 may not be necessary. In some embodiments, the user device 202 can also be equipped with a LiDAR sensor. The LiDAR sensor can be used to detect the visual indicators 210. In other cases, the LiDAR sensor can also scan the environment, and generate LiDAR sensor data which can be analyzed to identify objects or features corresponding to a patient's head. For example, the LiDAR sensor data can be used to identify recognizable landmarks on the patient's head (e.g., eyes, nose, mouth, ears, chin, and jaw), which, in turn, can help identify the patient's head position and orientation.

Referring now to FIG. 2B, there is shown a schematic representation of an example environment 200*b* for augmented reality visualization of BPPV, in accordance with some other embodiments.

As shown, the user device 202 may also be a head-mounted device that straps around the user's head. For example, as illustrated, the user device 202 is located inside a hands-free set which straps around the user's head using a head strap 206. In this configuration, the user's hands are freed for occupation with other functions. For example, the user 204 (e.g., a medical practitioner or physical therapist) can occupy their hands with applying a sequence of head and body maneuvers to the subject 208 while concurrently viewing the AR environment on user device display. The head-mounted device also provides the user 204 with a more immersive AR experience.

It will be appreciated that while the user device 204 has been illustrated herein as being either a hand-held device or a head-mounted device, the user device 202 can also be accessible to user 204 in any other manner. For example, the user device 202 can be mounted onto a stationary mount unit.

It will also be appreciated that the environments 200*a* and 200*b* may not necessarily include subject 208. For example, in some embodiments, the user device 202 can simply project virtual objects over any environment which surrounds the user 204. In still other cases, the virtual objects can be projected over an artificially generated environment (e.g., a simulated environment), generated by an AR application operating on the user device 202.

Figure 3:
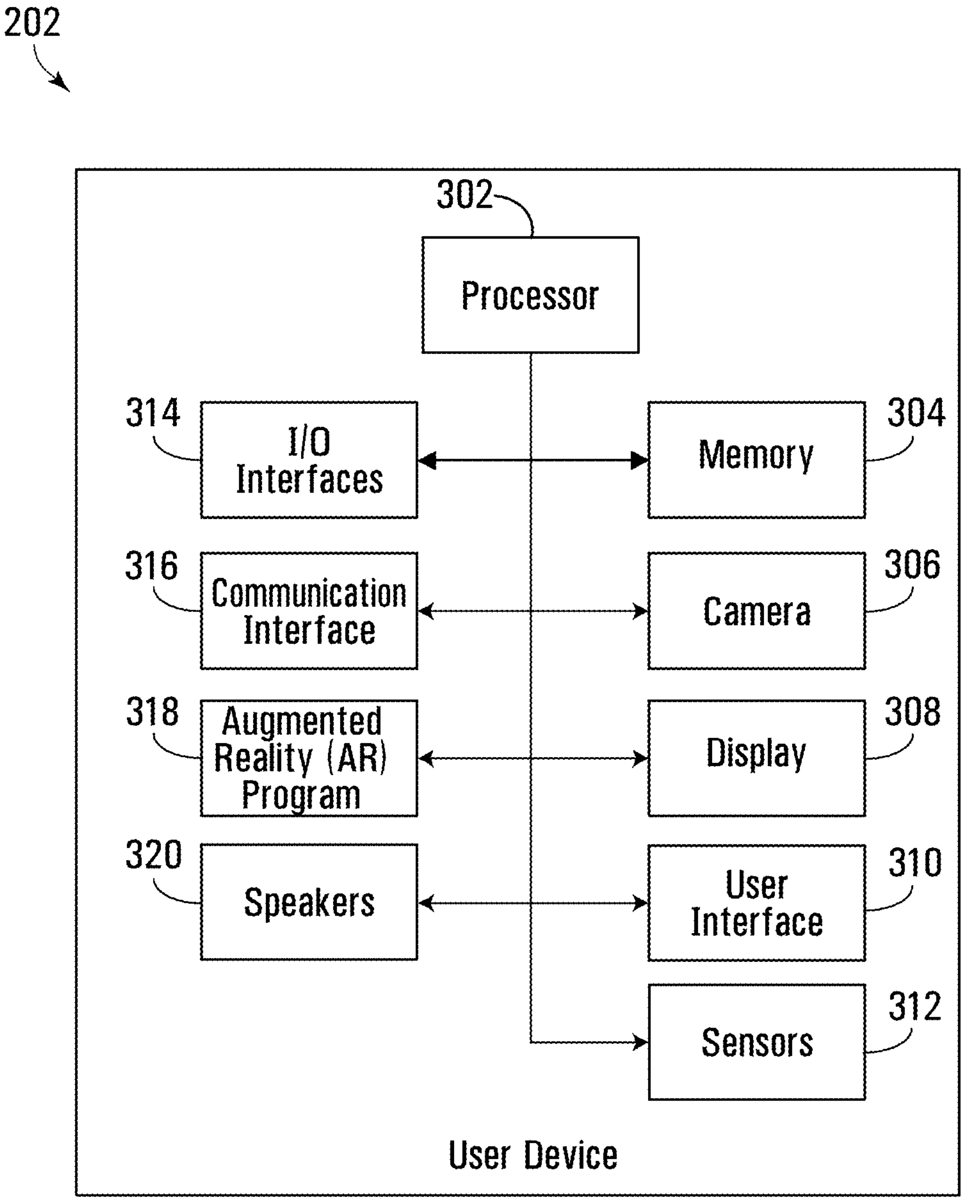
FIG. 3 is a block diagram of an example user device.

Referring now to FIG. 3, there is shown a simplified block diagram 300 of an example user device 202.

User device 202 may be, for example, a mobile user device (e.g., as shown in FIG. 2A) but may also include any suitable computing device capable of executing an application. For instance, user device 202 may also be a desktop or laptop computer, as well as a smartphones, tablet computers, as well as a wide variety of "smart" devices capable of data communication. Increasingly, this encompasses a wide variety of devices as more devices become networked through the "Internet of Things".

As shown, user device 202 may generally include a processor 302, a memory 304, a camera 306, a display 308, a user interface 310, sensors 312, an input/output (I/O) interface 314, a communication interface 316 and an augmented reality (AR) program 318. In various cases, user device 202 may also include speakers 320.

Processor 302 is a computer processor, such as a general purpose microprocessor. In some other cases, processor 302 may be a field programmable gate array, application specific integrated circuit, microcontroller, or other suitable computer processor.

Processor 302 is coupled, via a computer data bus, to memory 304. Memory 304 may include both volatile and non-volatile memory. Non-volatile memory stores computer programs consisting of computer-executable instructions, which may be loaded into the volatile memory for execution by processor 302 as needed. It will be understood by those of skill in the art that references herein to user device 202 as carrying out a function or acting in a particular way imply that processor 302 is executing instructions (e.g., a software program) stored in memory 304 and possibly transmitting or receiving inputs and outputs via one or more interfaces. Memory 304 may also store data input to, or output from, processor 302 in the course of executing the computer-executable instructions. In various cases, augmented reality (AR) program 318 may also be stored on memory 304.

Camera 306 is generally a digital camera, which captures digital images, or a digital video camera, which captures consecutive digital image frames. For example, as shown in FIGS. 2A and 2B, camera 306 may be configured to capture a real-time, or near real-time, digital video of a subject 208, or otherwise capture a digital video of a user's surrounding environment. In at least some cases, camera 306 may be integrated in user device 202, but may also be a separate device that is otherwise in communication with the user device 202. For example, in some cases, the camera 306 may be a separate device in wired or wireless communication with the user device 202 (e.g., via communication interface 316).

In at least some embodiments, camera 306 may be configured with infrared (IR) scanning functionality, and may include infrared photodetectors configured to detect heat radiation. In at least some cases, as explained in further detail herein, the IR information generated by camera 306 may be used to identify the location of specific objects located in a user's surrounding environment. For example, the IR information may be used to identify the location of a subject's head 208 in a captured image sequence. In other cases, the IR camera may be provided as a separate device in communication with user device 202.

Display 308 may be any suitable display for outputting information and data as needed by various computer programs. For example, display 308 may be a screen integrated in user device 202, or otherwise in communication with user device 202. In various cases, the display 308 may be configured to display an augmented reality or virtual reality environment for visualizing BPPV. For example, in various embodiments explained herein, display 308 may receive and display a video feed captured by camera 306 in real-time or near real-time of a user's surrounding environment. The display 308 may then display rendered virtual objects projected over the sequence of captured image frames. For instance, as explained herein, display 308 may display virtual models of example human inner ears projected over images frames captured by camera 306. In other cases, display 308 may also display a virtual (e.g., simulated) environment, and may project the virtual objects inside the virtual environment.

In at least some embodiments, display 308 may be a touch-screen display. For example, display 308 may be a resistive or capacitive touchscreen which is configured to detect touch force applied by a user 204 of user device 202. In various cases, this may allow a user 204 to use the touchscreen to interact with virtual objects displayed on display 308. In other cases, a separate input interface (e.g., keyboard and mouse) may be provided for receiving user inputs.

In some embodiments, display 308 may also display a graphical user interface (GUI). For example, as explained herein, the GUI may provide a user friendly environment for viewing and interacting with virtual objects and images displayed on display 308.

User interface 310 may be one or more devices that allow a user, or operator, to interact with the user device 202. For example, the user interface 310 may have a keyboard or other input device that allows a user to input instructions into the user device 202. For example, in various cases, the user may input instructions for camera 306 to capture a digital video of a user's surrounding environment. In other cases, the user interface 310 may allow the user to perform functions previously described with respect to the touchscreen display 308.

User device 202 may also include one or more sensors 312, which may be configured to detect motion of the user device 202. Sensors 312 may include, for example, an inertial measurement unit (IMU), which may include at least a gyroscope and one or more accelerometers. The IMU may be detect movement and rotation of the user device 202. For example, a user 204 may rotate the user device 202 to rotate the camera view. By rotating the camera view, the user may view, on display 308, different perspectives of a virtual model of an example inner ear which is projected on the user's surrounding environment (or a virtual environment). Accordingly, the IMU may detect rotation (and movement) of user device 202, and may transmit the rotational (and positional) information to AR program 318. The AR program 318 may receive the rotational (and positional) information from the IMU, and may update the displayed virtual model based on the received rotational (and positional) information. Accordingly, a user of user device 202 may perceive the virtual model from different perspectives by rotating (and moving) the user device. In other cases, sensors 312 can also include a LiDAR sensor. As explained herein, the LiDAR sensor can be used to identify visual indicators 210 attached to a patient's head. In other cases, generated LiDAR sensor data can also be used to identify recognizable features indicating the location and position of a patient's head.

Input/output (I/O) interface 314 may allow for coupling of other devices to the user device 204. For example, in some cases, the camera 306 and/or display 308 may not be integrated into the user device 202, and may be coupled to the user device 202 via I/O interface 314. In other cases, an integrated camera may not be configured with IR scanning functionality, and an IR camera may also be coupled to user device 202 via I/O interface 314.

Communication interface 316 may be one or more data network interface, such as an IEEE 802.3 or IEEE 802.11 interface, for communication over a network with other components.

Augmented reality (AR) program 318 may be, for example, a stand-alone application located on a mobile user device 202, or a program located on a desktop computer. In other cases, AR program 318 may be a plug-in or an extension for a web-browser interface located on user device 202.

AR program 318 may be configured to generate (e.g., render) and transmit virtual objects for display on display 308. The virtual objects may be rendered, for example, using data retrieved from memory 304 (e.g., data stored on memory 304), or otherwise, from data received from an external server in communication with user device 202 (e.g., via communication interface 316).

In various embodiments, the AR program 318 may operate in conjunction with the camera 306. For example, the camera 306 may capture a sequence of images (e.g., a digital video) in real-time—or near real-time—of a user's surrounding environment. The AR program 318 may receive the image sequence, and may render one or more virtual objects over the captured image sequence to generate an augmented reality environment. The images generated by the AR program 318 may then be transmitted for display on the display 308 in real-time, or near real-time. AR program 318 may also render (e.g., project) virtual objects over an artificial or simulated environment, which may also be generated by the AR program 318.

In some cases, virtual objects rendered by AR program 318 may include virtual models of example human inner ears. For example, AR program 318 may render a two-dimensional (2D), or a three-dimensional (3D) virtual inner ear model (e.g., an anatomical 3D model of the inner ear, as shown in FIG. 1). The rendered virtual inner ear model may allow a user 204 to better visualize and understand the anatomy of the human ear.

Figure 4A:
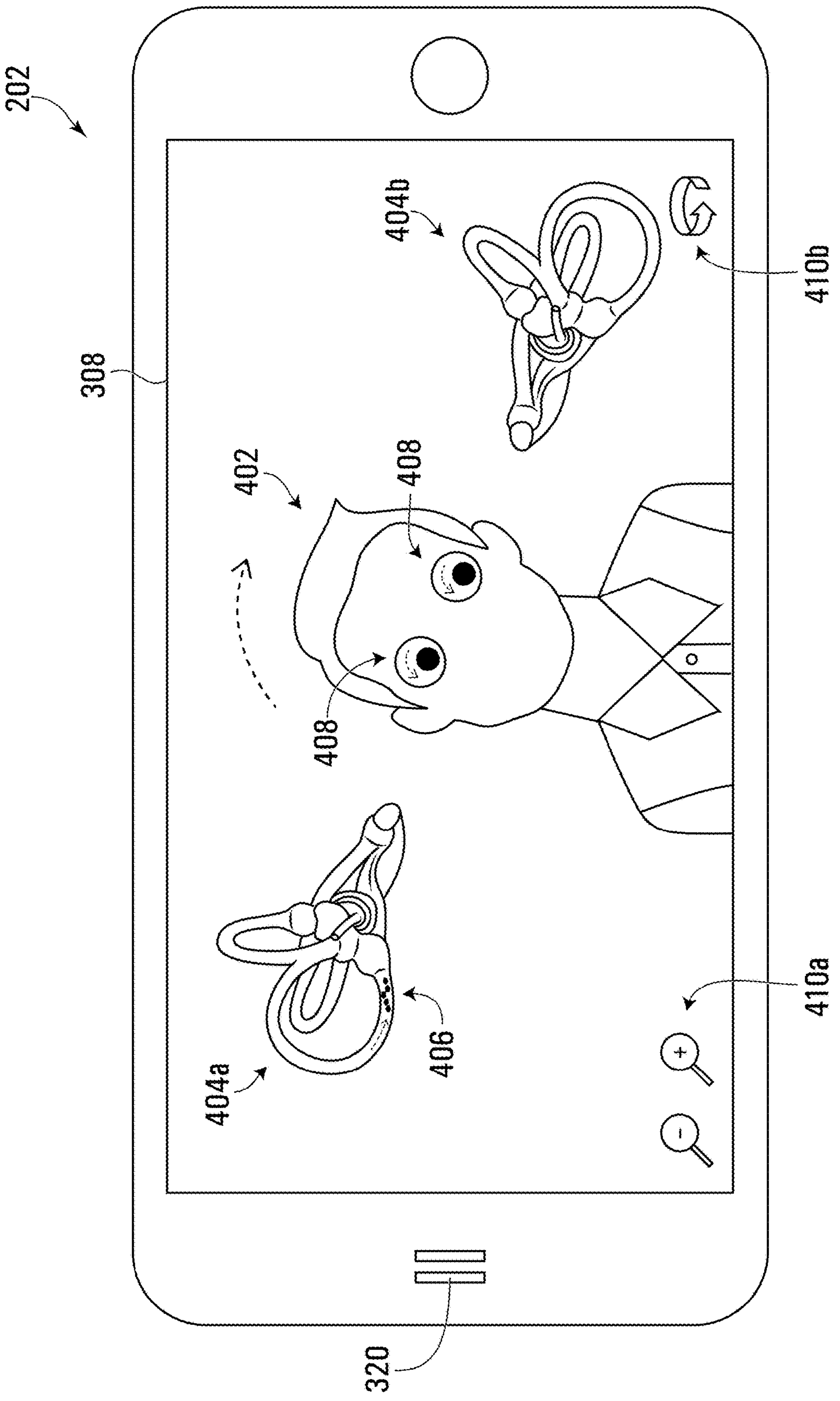
FIG. 4A is a display, of a user device, showing a simulated visualization of BPPV, according to some embodiments.
Figure 4B:
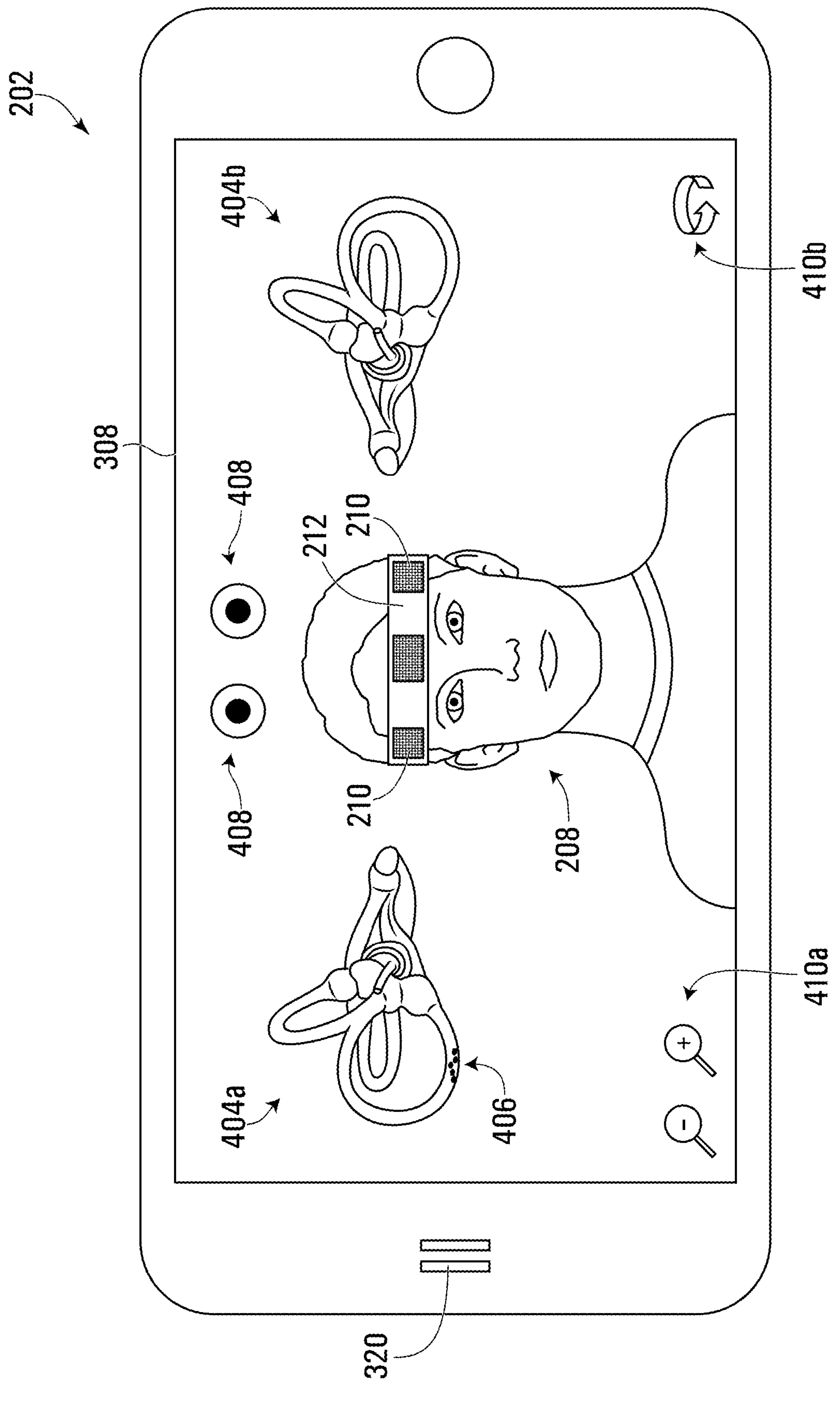
FIG. 4B is a display, of a user device, showing an example augmented reality visualization of BPPV, according to some other embodiments.
Figure 4C:
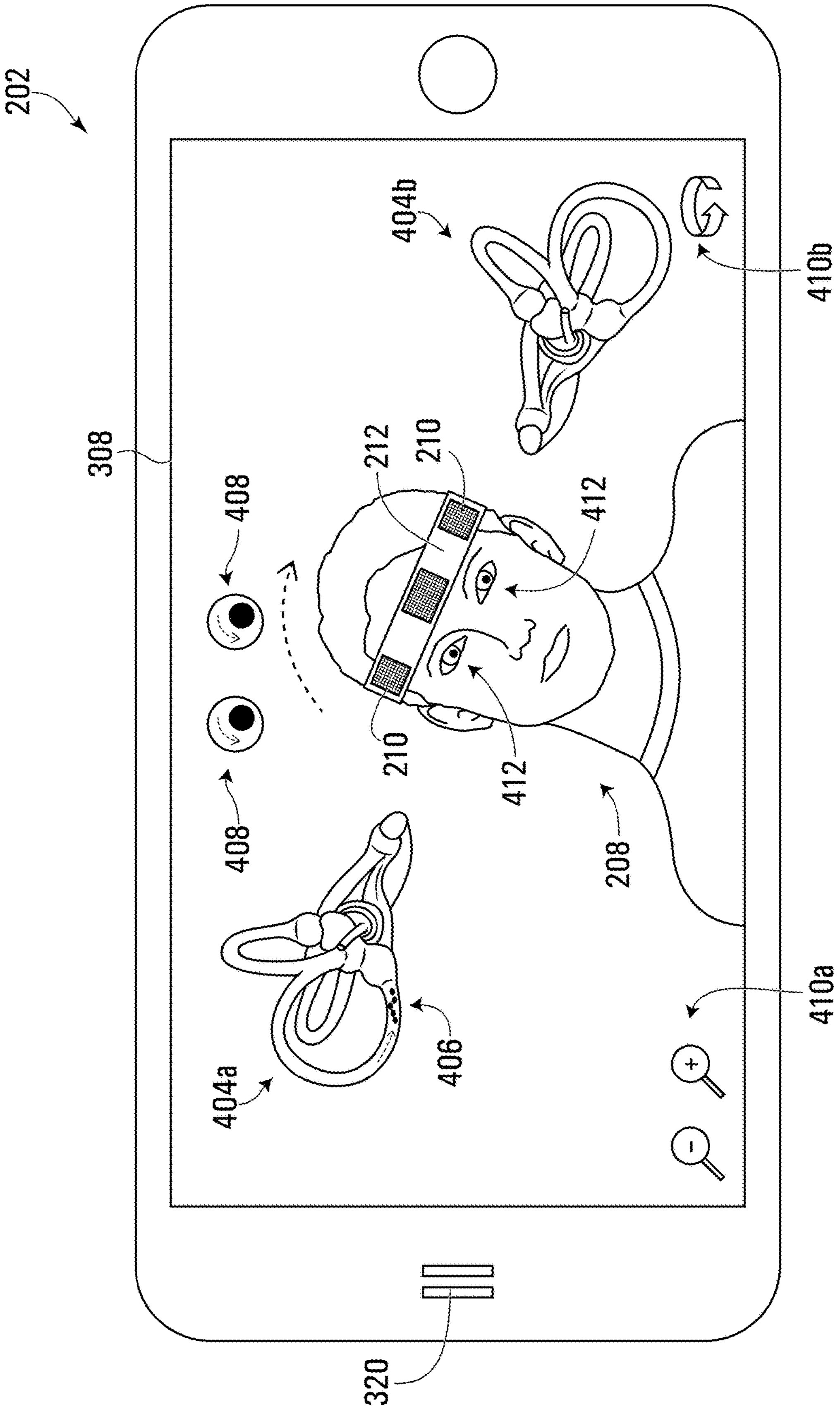
FIG. 4C is a display, of a user device, showing an example augmented reality visualization of BPPV, according to some further embodiments.

Referring now briefly to FIGS. 4A-4C, which show various example displays 308, of a user device 202. As shown in each of these figures, the AR program 318 may generate and render one or more inner ear models (e.g., a right inner ear model 404*a* and a left inner ear model 404*b*), for display on the display 308.

AR program 318 may also adjust features of the rendered virtual ear models. The features may be adjusted in response to user inputs (e.g., using a touchscreen display 308 or user interface 310), or otherwise automatically adjusted in response to certain user or patient actions.

For example, AR program 318 may adjust the number of ear models displayed on display 308. In other words, AR program 318 may render both a left inner ear model and a right inner model to allow a user to view different ear models. AR program 318 can also render only a desired portion of an inner ear model. Still further, AR program 318 can also render a plurality of left and/or right inner ear models. In some cases, this can allow a user to view different variations of inner ear models simultaneously. For example, a user may wish to view multiple ear models having virtual otoconia located in different positions as explained herein, or different ear models rotated in different positions.

AR program 318 may also adjust the transparency of virtual ear models. For example, virtual ear models may be made more transparent, or otherwise, more opaque. The virtual models may be made more transparent, for example, to allow viewing of the inner anatomy of the virtual ears. In some cases, AR program 318 may also generate different sectional views of the virtual models. For instance, AR program 318 may generate different cross-sectional views that allow a user to observe inside the ear. This feature may be provided in addition to, or in alternative to, adjusting the model transparency. The transparency and cross-sectional views of the ear models can be adjusted, for example, by a user using the user interface 310.

As explained herein, AR program 318 may also adjust the viewing perspective, or angular view, of a 3D virtual ear model. For example, AR program 318 can allow rotation of a virtual model in response to a received user input (e.g., the user may rotate the virtual ear model using a GUI interface on display 308). For example, FIG. 4A shows a GUI which includes a graphic element 410*a* for zooming-in or zooming-out of the virtual models 404, as well as a graphic element 410*b* for rotating one or more of the virtual models 404.

AR program 318 may also rotate the view of the ear models based on information received from sensors 312 (e.g., an IMU). For example, in some cases, the virtual models may be projected on an image sequence (e.g., digital video), captured by camera 306—in real-time or near real-time—and responsive to the user rotating the user device 202 (or the camera view of camera 306), AR program 318 can correspondingly adjust the displayed perspective view of the virtual model. For example, a user may move (e.g., rotate) the user device 202 around the subject's head, and the displayed perspective view of the ear models can correspondingly change in real-time, or near real-time, with movement of the user device 202 to show front, side and rear views. In still other embodiments explained herein, the AR program 318 may synchronize rotation of the virtual ear models with detected rotation of an actual subject's head.

Accordingly, it will be appreciated that the AR program 318 may vary a wide array of features relating to the virtual ear models in order to enhance user experience of the augmented reality or virtual environment.

In various cases, AR program 318 can also simulate BPPV. This can be done by displaying a set of virtual displaced otoconia inside of at least one rendered ear model. For example, the AR program 318 may generate a virtual ear model having virtualized otoconia located, for example, within a semi-circular canal. For examples, FIGS. 4A-4C shows example virtual otoconia 406 displayed inside of an ear model 404*a*.

The virtual otoconia can be rendered by the AR program 318 in different locations within the virtual ears, or in different ears (e.g., left or right). For example, AR program 318 may change the location of the virtual otoconia in response to receiving a user input (e.g., a user may change the location of the virtual otoconia using an input device). The location of the virtual otoconia can also be automatically adjusted by the AR program 318 in response to user or patient actions, as explained herein. Various other features of the virtualized otoconia can also be adjusted (e.g., size and shape). The AR program 318 can also toggle display of the virtual otoconia, e.g., as desired by the user.

To simulate BPPV, the AR program 318 may further visualize shifting (e.g., movement) of the displaced otoconia within the virtual ears. For example, AR program 318 may render the otoconia moving within the virtual inner ear, under the simulated effect of gravity (e.g., the virtual otoconia maybe coded with gravity properties). For example, virtual otoconia may move within the virtual ear in response to movement and rotation of the virtual ear. FIGS. 4B and 4C, for example, illustrate octonia 406 shifting within the ear model 404*a* in response to rotation of the ear model, and under the simulated effect of gravity.

When visualizing movement of the octoconia, AR program 318 may account for various factors which may affect the movement of the otoconia inside the ear. For example, the AR program 318 may account for fluid friction in the canals (e.g., viscous friction) which otherwise slow down the speed of movement of the otoconia. The AR program 318 may also account for friction between the otoconia and the inner wall of the canals, which may also effect the speed or direction of otoconia movement.

In some cases, AR program 318 may shift the otoconia inside of the virtual inner ear model in response to rotation of the inner ear models (e.g., by the user). Accordingly, this feature may allow a user 204 (e.g., a medical or physical therapy students) to observe how movement of the inner ear (e.g., resulting from head movement) influences shifting of the otoconia inside the ear. In some cases, a user 204 may move (e.g., rotate) the virtual models in different directions (e.g., using an input device), and may observe, on display 308, how each movement affects the shifting of the virtual otoconia. In at least some cases, a user 204 may also practice moving (e.g., rotating) the virtual ear models in order to guide the virtual otoconia within the ear to a desired location. For instance, a user may practice moving the ear model to guide virtual otoconia out of the semi-circular canals, and into the otolith organs. Accordingly, the virtual ear models may act as an assistive learning tool for students or inexperienced practitioners to better understand BPPV.

Referring now briefly to FIG. 4A, there is shown a display 308, of user device 202, showing a simulated visualization of BPPV, according to some embodiments.

As shown, in various cases, the AR program 318 may render the virtual ear models 404 in conjunction with an "avatar head" 402. The avatar head 402 may simulate, for example, a hypothetical patient affected by BPPV disorder.

The avatar head 402 may be displayed on display 308 in-between the pair of virtual ears 404 (e.g., a right virtual ear model 404*a* and a left virtual ear model 404*b*, or at least one ear model). The ear models 404 may be synchronized with movement of the avatar head 402. In the illustrated example, the avatar head 402 is rotated to the left by a user 204 of user device 202 (e.g., using a touchscreen display 308), and the virtual ear models 404 are also correspondingly rotated to the left. The right virtual ear model 404*a* is also illustrated with the set of virtual otoconia 406. As shown, the virtual otoconia 406 shifts within the virtual ear model 404*a*, under the simulated influence of gravity, as a result of the tilting of the avatar head 402. The avatar head 402 is also illustrated with a set of animated eyes 408 which are configured to simulate the effect of nystagmus, resulting from shifting of the virtual otoconia 406 inside the virtual ear 404*a*.

In various cases, the use of an avatar head 402 may allow users to understand how different head positions result in different movement of the virtual otoconia 406 inside the inner ear 404. The avatar head 402 may also enable users to learn to apply the correct sequence of head and body maneuvers for treating hypothetical cases of BPPV. For example, a user may move the avatar head 402 to guide the virtual otoconia 406 out of the virtual canals, and back into the otolith organs. Accordingly, the avatar head 402 may provide students and in-experienced practitioners, alike, with a simulated environment for learning to treat BPPV. As explained in further detail herein, in at least some cases, AR program 318 may also generate visual (e.g., textual or graphic), auditory or tactile instructions which may guide a user in treating the hypothetical case of BPPV using the avatar head 402.

Still referring to FIG. 4A, AR program 318 may also render a set of virtual animated eyes 408 on display 308. The animated eyes 408 may be, for example, displayed in conjunction with avatar head 402, or otherwise, separately (e.g., independently) from the avatar head 402 (e.g., the avatar head 402 may not be displayed, and only the eyes 408 may be displayed). The animated eyes 408 may, for example, replicate patterns of nystagmus. For example, the animated eyes 408 may display different eye movement patterns resulting from movement of the virtual otoconia 406 inside the virtual ear models 404. For instance, a user may move the virtual ear models 404 (or the avatar head 402) in order to shift the virtual otoconia 406, and may observe the resulting pattern of nystagmus on the animated eyes 408. Accordingly, this may allow users (e.g., students or in-experienced practitioners) to gain a better understanding of the relationship between patterns of nystagmus and movement of the otoconia within the inner ear.

The combination of the animated eyes 408, avatar head 402 and the virtual ear models 404 may, in various cases, serve as a testing tool for evaluating users ability to diagnose BPPV. For example, the AR program 318 may display the avatar head 402 in a pre-defined position (e.g., in a tilted position), and the animated eyes 408 may be made to follow a pre-defined pattern of nystagmus based on the avatar head's position. Further, the position of the virtual otoconia 406 may be hidden from view to the user. Based on the displayed avatar head position and the pattern of nystagmus, the user may be asked to predict a location for the virtual otoconia 406 inside the virtual ear model (e.g., using an input device). The AR program 318 may then display (e.g., automatically, or in response to a user input) the correct position for the virtual otoconia 406, thereby allowing the user to evaluate their ability to correctly analyze head positions and nystagmus patterns to correctly identify the location of the virtual otoconia within the inner ear.

Using the avatar head 402, AR program 318 can also allow users to test their ability to treat BPPV (i.e., in addition to diagnosing BPPV). For example, AR program 318 may display the avatar head 402, the animated eyes 408, and one or more virtual ear models 404. The AR program 318 may then momentarily display an initial position for the virtual otoconia 406 within at least one virtual ear model 404. The AR program 318 may then hide the display of the otoconia 406 within the virtual ear model 404 (or otherwise, the user may select to hide the otoconia from display). The user may then be asked to apply a sequence of maneuvers to the avatar head 402 (or the virtual ear models 404) to treat the simulated case of BPPV. After completing the sequence of movements, the AR program 318 may then display the final location of the virtual otoconia 406 resulting from the sequence of movements applied to the avatar head 402. Accordingly, a user may observe the final position of the otoconia to determine whether they have applied the correct sequence of maneuvers which properly guide the virtual otoconia 406 back into the otolith organs.

In view of the foregoing, it will be appreciated that the combination of the animated eyes 408, avatar head 402 and the virtual ear models 404 may provide for a beneficial tool for understanding BPPV, as well as for evaluating the ability of a user to diagnose and treat BPPV.

Referring now briefly to FIGS. 4B and 4C, there are illustrated various example displays 308, of user device 202, showing various simulated visualizations of BPPV, according to some other embodiments.

As shown, AR program 318 may also be configured to position virtual ear models 404*a*, 404*b* over captured images of an actual subject patient's head 208. In particular, as explained herein, this feature may allow the AR program 318 to assist practitioners in real-time diagnosis and treatment of actual subjects suffering from BPPV. For example, camera 306—of user device 202—may capture an image sequence of subject 208 (e.g., a digital video)—in real-time or near real-time. AR program 318 may receive the image sequence, and relatively position virtual models of a right inner ear 404*a* and a left inner ear 404*b* over the image of the subject's head.

In order to synchronize the rendered virtual ear models 404 with the subject's head 208 (e.g., for synchronized movement or rotation), visual indicators 210 may be positioned on the subject 208. For example, visual indicators 210 may be located on a head band 212 placed around the subject's forehead. In other cases, the visual indicators 210 may be located in any other region of the subject's head or body, and may be attached to the subject in any other suitable manner. The visual indicators 210 may be, for example, a scannable pattern such as a two-dimensional barcode, a quick response (QR) code, or a visual text or design. The AR program 318 may receive and analyze an image, or image sequence (e.g., digital video) from the camera in order to identify and determine the location of the visual indicators 210. In other cases, the visual indicators 210 may be automatically detected by one or more sensors 312 (e.g., LiDAR sensors detecting unique LiDAR-detectable QR codes). Based on the identification of the visual indicators 210, the AR program 318 may locate the user's head in the image, and may relatively position the virtual ear models to the subject's head on display 308. In various cases, the visual indicators 210 may be positioned to allow the AR program 318 to identify the Reid's line of the patient 208, and to position the virtual ear models 404*a*, 404*b* in respect of the Reid line. For example, the visual indicators 210 may be positioned along a plane of, or slightly offset by a pre-determined distance from the plane defining the Reid's line. The AR program 318 may then position the virtual ear models at the same plane as visual indicators, are at a pre-defined offset distance known to the AR program 318.

In other cases, in addition to or in the alternative of using visual indicators, the AR program 318 may work in conjunction with other image processing programs located on the user device 202 to analyze an image or digital environment representation to identify—in the captured image—pre-determined shapes corresponding to a patient's head, as well as identifiable anatomical features (e.g., eyes, nose, ear, chin, etc.) which indicate head orientation and position. In some cases, the AR program 318 (or other suitable programs) may be pre-programmed (e.g., pre-trained) to identify known features corresponding to a patient's head, as well as to various known anatomical features.

The AR program 318 may also identify the location and orientation of a user's head in an image based on IR data received from an IR scanner. For example, the camera 306 may be configured with IR scanning functionality, or in other cases, an IR camera may be coupled to I/O interface 314 of user device 202. The AR program 318 may receive thermal imaging data from the IR scanner, and may use the thermal imaging data to locate the position of the subject's head in the image sequence, as well as identifiable anatomical features (e.g., eyes, nose, ear, chin, etc.) which indicate head orientation and position. In still other embodiments, the location and orientation of the user's head can be determined based on data received from other sensors 312. For example, data generated by a LiDAR sensor (or other time-of-flight sensors included in sensors 312) can be analyzed by the AR program 318 to detect recognizable shapes corresponding to a patient's head, as well as distinctive anatomical features (e.g., eyes, nose, ear, chin, etc.), which can be used to determine head position and orientation.

As shown in FIG. 4C, the AR program 318 may also synchronize the position and rotation of the virtual ear models 404*a*, 404*b* with the detected movement of the subject's head 208 (e.g., based on detect movement of visual indicators 210). For example, the AR program 318 may analyze image frames to detect movement of the subject's head (e.g., via detecting movement of the visual indicators 210 in the images, or through image analysis to determine movement of a head shape/anatomical features in the images), and may re-position (e.g., move) and rotate the virtual ear models 404*a*, 404*b* in synchronization with the subject's head on display 308. In other cases, head movement can also be detected based on IR or LiDAR sensor data. In particular, as shown in FIG. 4C, subject 208 has rotated (e.g., tilted) their head to the left. For instance, the subject may have tilted their head in response to instructions received from a medical practitioner or physical therapist (e.g., user 204). The head rotation is detected by AR program 318, and the AR program 318 may accordingly re-position and rotate the virtual ear models 404 to synchronize the orientation of the virtual ear models with the detected head rotation.

In some embodiments, as the virtual models 404*a*, 404*b* are re-oriented (e.g., tilted) in response to movement of the subject's head, the AR program 318 can also display shifting of the virtual otoconia 406 inside the virtual ear models. This feature may provide a user (e.g., a medical practitioner or physical therapist), for example, with a visual guide for treating the subject 208 diagnosed with BPPV.

In some cases, the AR program 318 may allow a medical practitioner to apply a sequence of maneuvers to an actual subject's head, all the while, tracking shifting of the virtual otoconia 406 inside the virtual ear models 404 based on display 308. Accordingly, observing the shifting of the virtual otoconia 406 may assist the practitioner in applying the correct sequence of maneuvers which move the otoconia out of the canals and back into the otolith organs. In this manner, the augmented reality environment may provide an assistive tool for more effective treatment of BPPV.

As shown in FIG. 4C, AR program 318 can also generate a set of animated eyes 408, to be displayed on display 308, in conjunction with the image sequence of the subject's head. The set of animated eyes 408 may display, for example, patterns of nystagmus resulting from movement of virtual otoconia 406 inside the synchronized virtual ear models. A user (e.g., a medical practitioner or physical therapist), of user device 202, may observe the animated pattern of nystagmus, and compare the animated pattern of nystagmus to the actual subject's nystagmus (e.g., 412 in FIG. 4C).

Where the animated and actual pattern of nystagmus are not identical, the virtual ear models 404*a*, 404*b* may be deemed inaccurate. This can occur, for example, where the virtual otoconia 406—inside the virtual ear models 404*a*, 404*b*—incorrectly reflect the actual position of the otoconia inside the actual patient subject's inner ear. To correct for this problem, the user 202—of user device 204—can adjust the virtual model by re-positioning the virtual otoconia. Accordingly, the animated eyes 408 may be used for verifying the accuracy of the virtual ear models 404*a*, 404*b*.

In other cases, the AR program 318 may analyze an image sequence to determine the actual subject's pattern of nystagmus. For example, the AR program 318 may include an image analysis feature which analyzes received images to determine movement of the subject's eyes. In other cases, the AR program 318 may cooperate with a separate application which analyzes images to identify eye movement in an image sequence of a subject. Based on the identified pattern of eye movement, the AR program 318 may update the position of the virtual otoconia 406 inside the virtual ear to reflect the correct position of the otoconia inside the subject's ear. Accordingly, the AR program 318 may be automatically configured to correct the virtual ear model with no input from a user.

Referring now back to FIG. 3, user device 202 may also include speakers 320. Speakers 320 can be used to provide auditory instructions to a user 204, of user device 202, for treating a case of BPPV. For example, as shown in FIG. 4A, the speakers 320 may provide instructions to a user (e.g., a medical student) for treating a simulated case of BPPV using the avatar head. Accordingly, the user may follow the auditory guidance to perform the correct sequence of maneuvers to the avatar head in order to guide the virtual otoconia 406 to a desired location. In other cases, the auditory instructions may assist a user (e.g., a medial practitioner or physical therapists) in treating an actual patient 208, as shown in FIGS. 4B and 4C. For instance, the instructions may guide the practitioner in applying the correct sequence of movements to subject 208 in order to guide the virtual otoconia to the otolith organs, and accordingly, treat the subject patient. In various cases, the auditory instructions may be generated by the AR program 318.

In other cases, as explained previously, the instructions may also be visual (e.g., textual or graphical instructions on display 308), or tactile.

Figure 5:
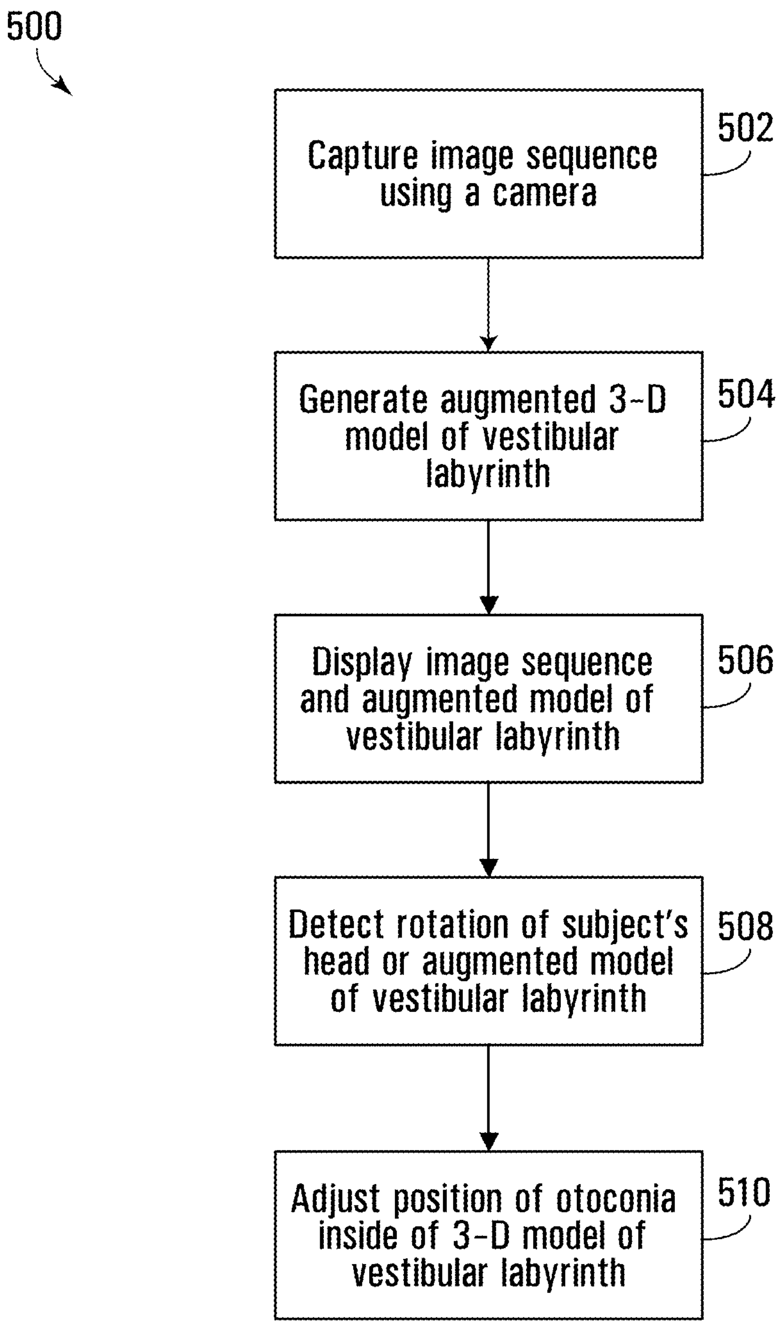
FIG. 5 is an example process flow for augmented reality visualization of BPPV.

Referring now to FIG. 5, there is shown an example process flow for a method 500 for augmented reality visualization of BPPV. The method 500 may be carried out, for example, using the processor 302 of the user device 202.

At 502, the camera 306 may be used to capture an image sequence of a subject 208 (e.g., a digital video).

At 504, the AR program 318 may receive the image sequence in real-time or near real-time, and may locate and determine the position of the subject's head 208 in the image sequence. For example, the AR program 318 may identify visual indicators 210 located on the subject's head which identify the position of the subject's head in the image sequence. In other cases, the AR program 318 may receive information from an IR scanning device (e.g., integrated into camera 306, or otherwise separately provided and in communication with user device 202). In still other cases, the AR program 318 may be configured—alone and/or in conjunction with a separate image analysis application—to analyze the received images to identify an image object that corresponds to the subject's head, as well as other image objects that correspond to other anatomical features of the head. In still yet other cases, the AR program 318 may locate the position of the subject's head, as well as various anatomical features, based on other received sensor data (e.g., LiDAR sensor data).

At 506, the AR program 318 may project (e.g., render) one or more virtual inner ear models, relatively positioned to the located image of the subject's head, in the image sequence in real-time, or near real-time. For example, the AR program 318 may render a right virtual inner ear model to the right of the subject's head, and a left virtual inner ear model to the left of the subject's head. In some cases, at least one or both of the virtual ear models may include a virtual set of otoconia. The AR program 318 may also render a set of animated eyes over the image of the subject's head.

At 508, the AR program 318 may detect rotation or head movement of the actual subject's head in the image sequence. For example, the head rotation or movement may be detected by tracking the movement of the visual indicators 210 within the received image sequence. For example, this can occur using an image analysis program which is configured to detect a recognizable and known pattern associated with the visual indicators 210. In other cases, the visual indicators 210 can be tracked based on other sensor data (e.g., LiDAR sensor data, or other time-of-flight sensor data). In still other cases, the head rotation or movement may be detected based on information received from an IR scanning device, or otherwise from LiDAR sensor data (or other time-of-flight sensor data).

At 510, the AR program 318 may adjust the virtual ear models to synchronize with the subject's head movement or rotation. For example, the virtual ear models may be rotated in synchronization with the actual subject's head rotation. In various cases, the virtual otoliths may also be shifted within the virtual ear model, under the simulated effect of gravity, in response to the rotation of the virtual ear models. In still other cases, the set of animated eyes may display a predicted (or expected) pattern of nystagmus, based on the shifting of the virtual otoconia inside the virtual ear model.

The present invention has been described here by way of example only, while numerous specific details are set forth herein in order to provide a thorough understanding of the exemplary embodiments described herein. However, it will be understood by those of ordinary skill in the art these embodiments may, in some cases, be practiced without these specific details. In other instances, well-known methods, procedures and components have not been described in detail so as not to obscure the description of the embodiments. Various modifications and variations may be made to these exemplary embodiments without departing from the spirit and scope of the invention, which is limited only by the appended claims.

The invention claimed is:

1. A system for augmented reality visualization of benign paroxysmal position vertigo (BPPV) disorder, the system comprising:
- a camera configured to capture an image sequence, wherein the image sequence includes an image of a subject's eyes;
- a processing unit configured to:
  - generate at least one virtual model of an inner ear, wherein the at least one virtual model of the inner ear comprises an accurate anatomical representation of a real human inner ear;
  - generate a simulated nystagmus pattern corresponding to movement of a set of virtual displaced otoconia within the at least one virtual model of the inner ear; and
- a display configured to:
  - display the at least one virtual model of the inner ear over the image sequence; and
  - display an augmented set of animated eyes that visually display the simulated nystagmus pattern in conjunction with or separately from the image sequence of the subject's eyes for visual comparison.

2. The system of claim 1, wherein the image sequence includes an image of a subject's head.

3. The system of claim 1, wherein the at least one virtual model of the inner ear includes the set of virtual displaced otoconia coded with gravity properties.

4. The system of claim 3, wherein the at least one virtual model of the inner ear comprises a first virtual model of a right inner ear and a second virtual model of a left inner ear, and the processing unit is configured to transmit instructions for the display to display the first virtual model on a right side of the image of the subject's head, and the second virtual model on the left side of the image of the subject's head.

5. The system of any one of claim 4, wherein the processing unit is further configured to monitor a movement of the subject's head in the image sequence, and is configured to generate a new orientation for the at least one virtual model based on the monitored movement of the subject's head, and the display is configured to display the new orientation of the at least one virtual model.

6. The system of claim 5, wherein the processing unit is configured to generate a new position for the virtual displaced otoconia inside the at least one virtual model of the inner ear, the new position for the displaced otoconia is based on the new orientation of the at least one virtual model of the inner ear, and wherein the display is configured to display the new position of the virtual displaced otoconia based on the coded gravity properties.

7. The system of claim 6, wherein the processing unit is further configured to generate the augmented set of animated eyes, and the display is configured to display the augmented set of animated eyes over the image sequence, the augmented set of animated being configured to follow a predetermined motion pattern based on a movement of the virtual displaced otoconia inside the at least one virtual model of the inner ear.

8. The system of claim 5, wherein the processing unit is configured to monitor a movement of the subject's head in the image sequence based on a visual indicator located on the image of the subject's head.

9. The system of claim 8, wherein the camera further comprises an infrared (IR) scanning capability, and the processing unit is configured to monitor the movement of the subject's head in the image sequence based on information generated by the IR scanning capability of the camera.

10. The system of claim 5, wherein the processing unit is configured to monitor a movement of the subject's head based on data generated by a time of flight sensor.

11. A method for generating an augmented reality model of at least one vestibular labyrinth, the method comprising:

capturing an image sequence using a camera, wherein the image sequence includes an image of a subject's eyes;

using a processing unit, generating at least one virtual model of an inner ear, wherein the virtual model of the inner ear comprises an accurate anatomical representation of a real human inner ear;

using a processing unit, generating a simulated nystagmus pattern corresponding to movement of a set of virtual displaced otoconia within the at least one virtual model of the inner ear;

displaying at least one virtual model of the inner ear over the image sequence; and displaying an augmented set of animated eyes that visually display the simulated nystagmus pattern in conjunction with or separately from the image sequence of the subject's eyes for visual comparison.

12. The method of claim 11, wherein the image sequence includes an image of a subject's head.

13. The method of claim 12, wherein the at least one virtual model of the inner ear includes the set of virtual displaced otoconia which are coded with gravity properties.

14. The method of claim 13, wherein the at least one virtual model of the inner ear comprises a first virtual model of a right inner ear and a second virtual model of a left inner ear, and the method further comprises transmitting instructions for the display to display the first virtual model on a right side of the image of the subject's head, and the second virtual model on the left side of the image of the subject's head.

15. The method of claim 14, further comprising monitoring a movement of the subject's head in the image sequence, and generating a new orientation for the at least one virtual model based on the monitored movement of the subject's head, and displaying the new orientation of the at least one virtual model.

16. The method of claim 15, further comprising generating a new position for the virtual displaced otoconia inside the at least one virtual model of the inner ear, the new position for the displaced otoconia is based on the new orientation of the at least one virtual model of the inner ear, and displaying the new position of the virtual displaced otoconia is based on the coded gravity properties.

17. The method of claim 16, further comprising generating the augmented set of animated eyes, and displaying the augmented set of animated eyes over the image sequence, the augmented set of animated eyes being configured to follow a predetermined motion pattern based on a movement of the virtual displaced otoconia inside the at least one virtual model of the inner ear.

18. The method of claim 15, further comprising monitoring a movement of the subject's head in the image sequence based on a visual indicator located on the image of the subject's head.

19. The method of claim 18, wherein the camera further comprises an infrared (IR) scanning capability, and the method further comprises monitoring movement of the subject's head in the image sequence based on information generated by the IR scanning capability of the camera.

20. The method of claim 15, further comprising monitoring a movement of the subject's head based on generated by a time-of-flight sensor.

* * * * *